US005604813A

United States Patent [19]

Evans et al.

[11] Patent Number: 5,604,813

[45] Date of Patent: Feb. 18, 1997

[54] INDUSTRIAL HEADSET

[75] Inventors: Robert D. Evans; John Roeder, both of Baltimore; Michael J. Burke, Annapolis; George W. Tye, Sykesville; William J. Hoge, Westminster, all of Md.

[73] Assignee: Noise Cancellation Technologies, Inc., Linthicum, Md.

[21] Appl. No.: 236,848

[22] Filed: May 2, 1994

[51] Int. Cl.[6] .......... A61F 11/06

[52] U.S. Cl. .......... 381/71; 381/94

[58] Field of Search .......... 381/71, 94, 72, 381/183; 455/149

[56] References Cited

U.S. PATENT DOCUMENTS

| | | | |
|---|---|---|---|
| 3,906,160 | 9/1975 | Nakamura et al. | 381/25 |
| 4,527,282 | 7/1985 | Chaplin et al. | 381/71 |
| 4,622,440 | 11/1986 | Slavin | 381/68.2 |
| 4,644,581 | 2/1987 | Sapiejewski | 381/74 |
| 4,985,925 | 1/1991 | Langberg | 381/72 |
| 4,987,592 | 1/1991 | Flagg | 381/183 |
| 5,182,774 | 1/1993 | Bourk | 381/71 |
| 5,361,304 | 11/1994 | Jones et al. | 381/71 |

*Primary Examiner*—Edward L. Coles, Sr.
*Assistant Examiner*—Jerome Grant, II
*Attorney, Agent, or Firm*—Daniel DeJoseph

[57] ABSTRACT

This invention relates to the various features of a headset design that utilizes active noise cancellation. This particular design has been developed to work with radio communication systems, but many features are applicable to headsets designed solely for ear protection. The unique design features of the invention allow for uninterrupted communication capability with active noise cancellation. The design also provides it own built in rechargeable power supply that is easily removed for recharging.

12 Claims, 14 Drawing Sheets

FIG. 6B
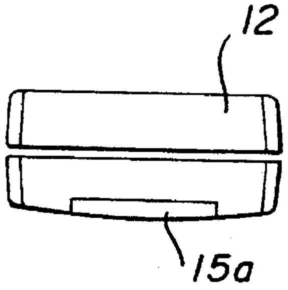
FIG. 6C
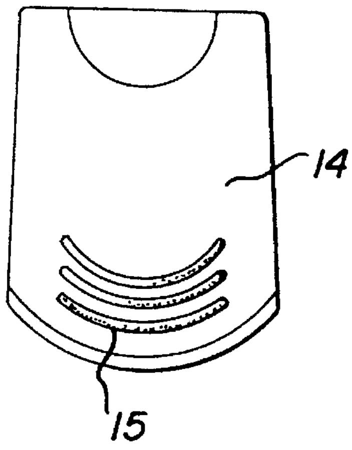
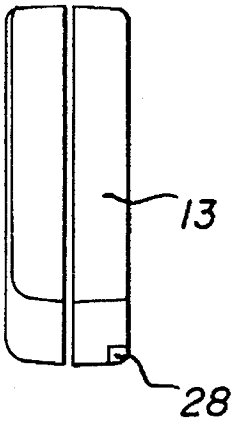
FIG. 6A

INDUSTRIAL HEADSET

This invention relates to an industrial headset that utilizes active noise reduction (ANR) to both protect the wearer's hearing and to work in conjunction with radio communication systems. The unique features of this invention including its circuitry allow for uninterrupted communication capability with ANR. A further feature includes a built-in detachable power supply that is designed for fast recharging in a rapid recharger.

BACKGROUND

The use of active noise cancellation in headsets has been utilized for some time. For example, U.S. Pat. No. 4,644,581 shows the use of a microphone and driver transducer in a headset designed to attenuate transmitted noise by counter noise. Langberg in U.S. Pat. No. 4,985,925 shows ANR in an earplug having multiple feedback loops.

Perhaps the first use of a speaker and microphone in an acoustically close volume was discussed and shown in Chaplin, U.S. Pat. No. 4,527,282.

Several other patents exist relating to the use of active noise cancellation in head sets. One example includes the work done by Bourk, U.S. Pat. No. 5,182,774, in which cancellation is achieved with the use of low, high, and mid range filters, and where the microphone is located coaxial with the driver (i.e., speaker). This invention differs from that device in several ways. Firstly, the circuitry includes a low pass filter and two band pass filters instead of mid and high pass filters. Secondly, this invention also includes a unique bridge circuit that bypasses the noise cancellation circuitry when the active system is turned off. Thirdly, this invention includes a booster circuit to compensate for low frequency losses when active noise cancellation is in operation. Fourthly, this invention does not require or implement coaxial location of the microphone element and the driver.

GENERAL DESCRIPTION

The present invention utilizes various features which are unique in its overall unique configuration. The arrangement facilitates the use of a two-way communication system without the loss of hearing protection or communication function.

The uninterrupted communication function of the head set is made possible by the implementation of a bridge circuit to form a directional coupler that minimizes feed back and allows direct drive to the speakers from the communication system. A boost circuit is placed in line with the audio communication link to offset any signal losses resulting from the application of active noise reduction. The present invention also features a built-in power supply that allows the noise cancellation of the headset to function independent of the communication system. The present invention utilizes an electronic design that is simple and inexpensive to implement, making it possible for the first time to provide a headset with active noise cancellation at consumer prices. Application for such a system will be largely in the area of heavy industry, and in air transportation (pilots, ground crews, air traffic control), although light weight open back versions are currently under development that would be used in telephone and multi-media applications.

Accordingly, it is an object of this invention to provide an industrial active noise reduction headset of unique design and wide application.

Another object of this invention is to provide an ANR headset for use with a two-way communications system.

A further object of this invention is to provide a communications headset for aviation that employs ANR.

A still further object of this invention is to provide a unique powering feature for headsets.

Yet another object of this invention is to provide an ANR headset having an innovative circuit design that minimizes feedback and allows direct drive to the headset speakers from a communications system.

Still another object of this invention is to provide a communications headset with ANR wherein the ANR operates independently of the communications system.

A further object of this invention is to provide an ANR headset for communications wherein a boost circuit is placed in line with the audio link to offset signal losses due to ANR.

These and other objects will become apparent when reference is had to the accompanying drawings in which:

FIG. 1 is a plan view of the headset of this invention as shown on a variety of different sized heads, FIG. 2 is a side view of the headset showing the battery pack, FIG. 3 is a side view opposite from FIG. 2 showing the boom microphone attachment, FIG. 4 is a rear view of the headset, FIG. 5 is a bottom view of the headset, FIG. 6 is a plan, top and side view of the battery pack, FIG. 7 is an exploded view of the active noise reduction portion of each earcup, FIG. 8 shows an exploded view of the right earcup which houses the removable battery pack, FIG. 9 shows an exploded view of the left earcup showing attachment of the boom microphone, FIG. 10 shows a perspective view of the headstrap portion of the headset, FIG. 11 shows a perspective view of the lower earcup portions of the headset with an exploded view of the right earcup, FIG. 12 is a block diagram of the acoustic feedback circuit, FIG. 13 is a block diagram of the bridge circuit, and FIG. 14 is the overall circuit diagram for the left side of the headset which is identical to the right side of the headset.

DETAILED DESCRIPTION

Figure 1:
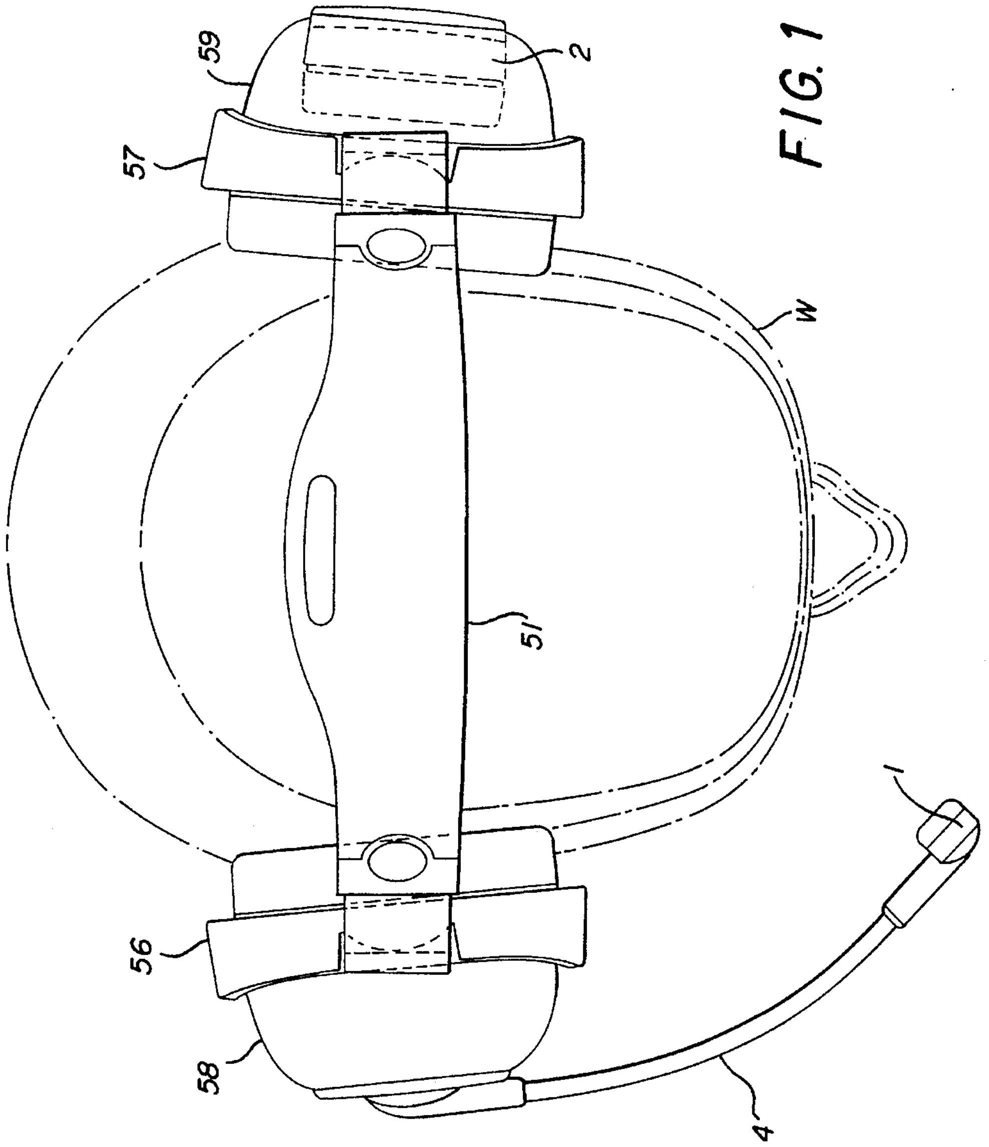

FIG. 1 shows a top down view of the proposed head set as it would rest on the user's head W. This design differs with many headsets in that the boom microphone 4 is shorter and less obtrusive than units that have the microphone placed directly in front of the user's mouth. It has a microphone 1 at its end. A rechargeable battery pack 2 also differentiates the proposed headset from other designs, which require the wearer to carry a belt pack power supply. The location of the battery pack 2 is in the right earcup where it can be easily removed for recharging and replaced with a newly charged unit. This allows the wearer to change battery packs without removing the headset.

Figure 2:
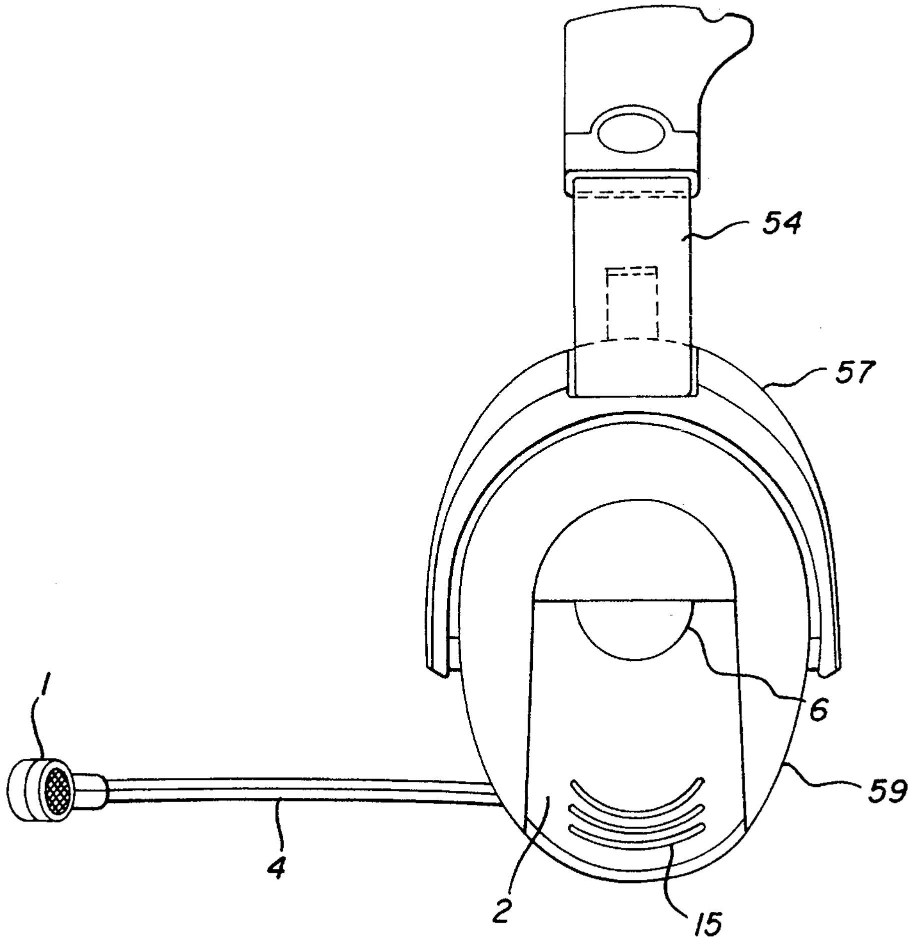

In FIG. 2 there is shown a side view of the head set which illustrates the removable battery pack 2. This allows the user to operate the headset without being encumbered with additional wiring. The "tear drop" shape of the earcups is also shown. The battery pack is held in by a latch portion 6 of the earcup 59 which can be flexed to allow removal of the battery pack.

Figure 3:
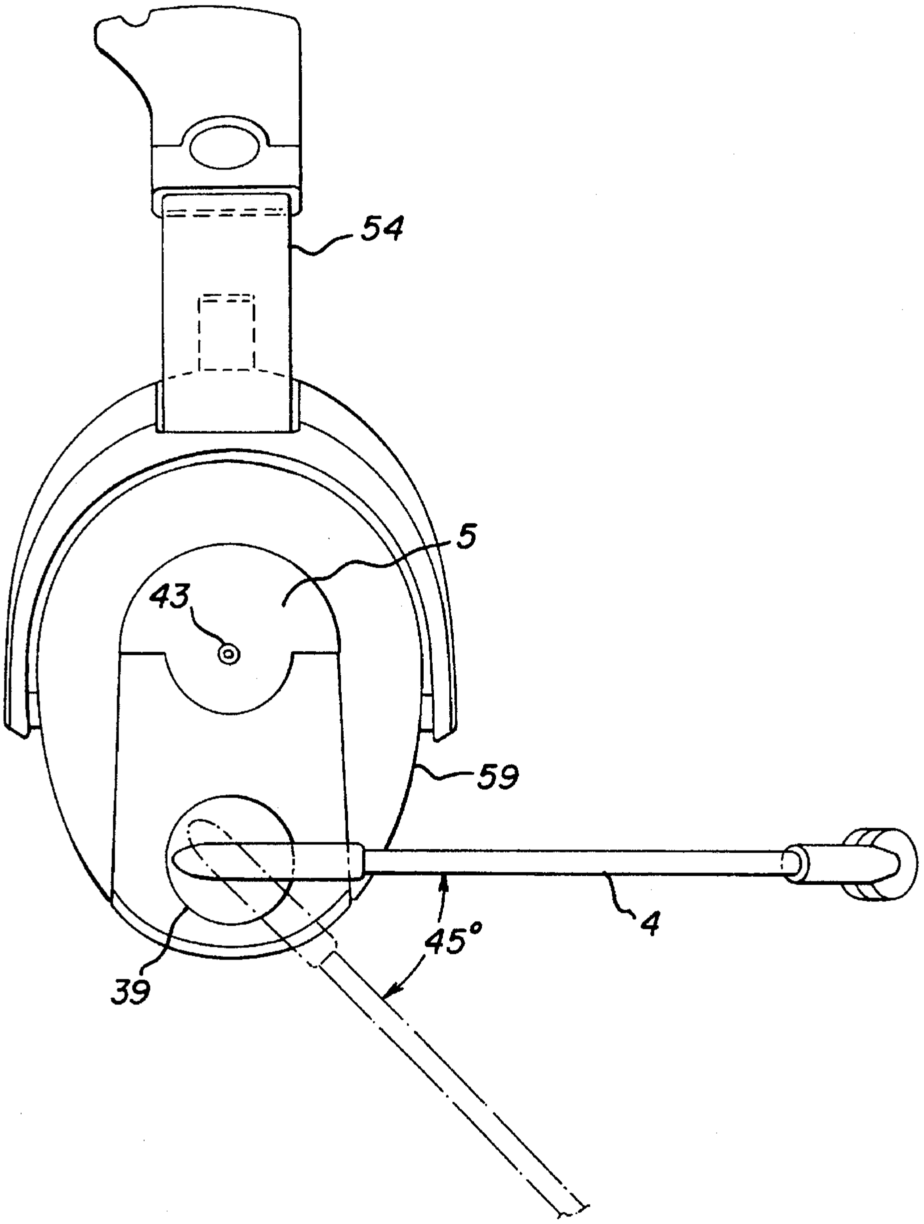

FIG. 3 illustrates the left side of the headset showing the full 45° of motion of the boom microphone 4. Also illustrated is the location of the light emitting diode (LED) 43, which indicates when the active noise reduction is in operation. The "tear drop" shape of the earcups is again illustrated in FIG. 3.

Figure 4:
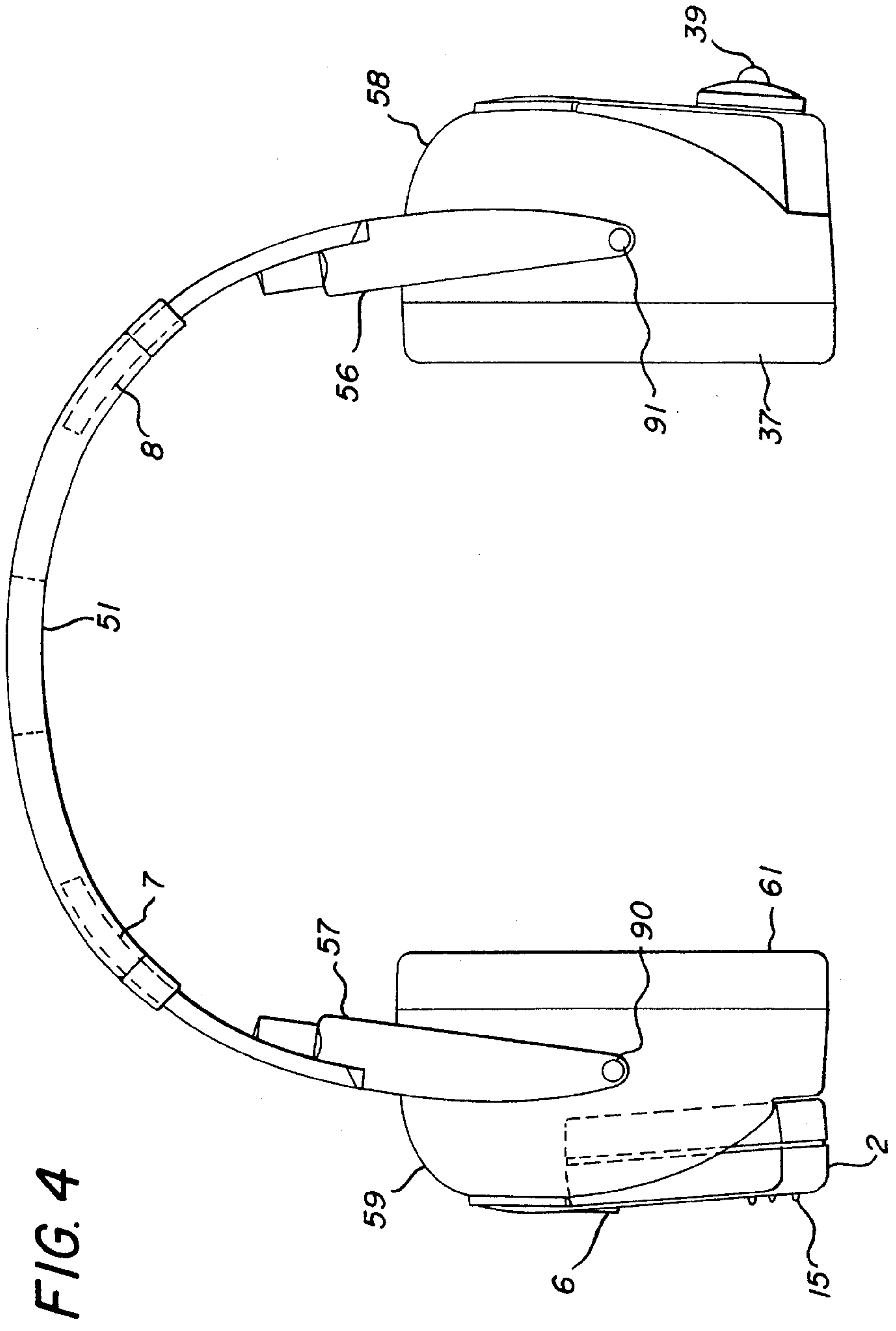

A back view of the headset is shown in FIG. 4. The dashed lines illustrate the sliding assembly that allows for adjustment of the headset. The extensions 7, 8 frictionally fit within headband 51 so as to allow the adjustment.

Figure 5:
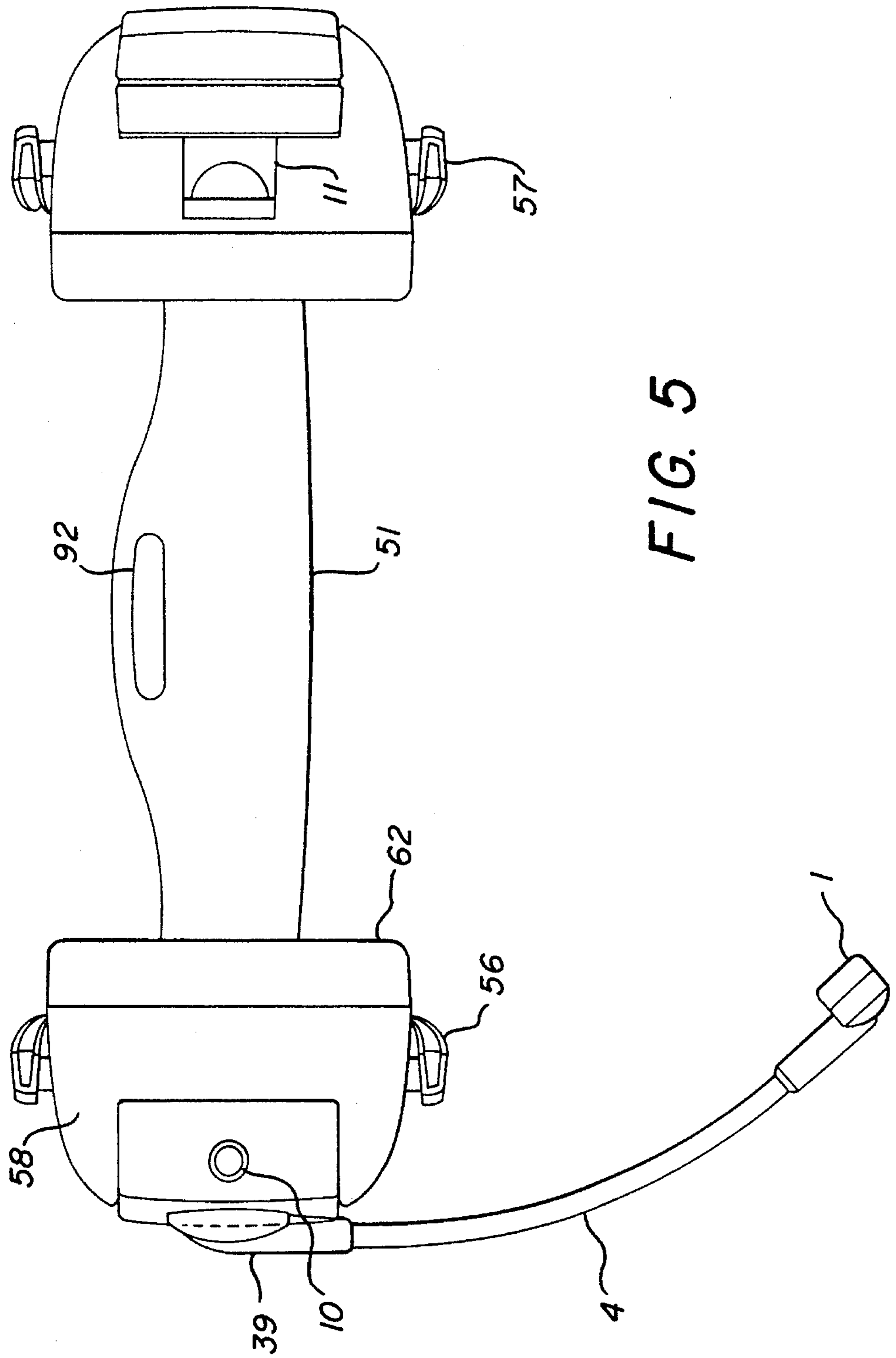

FIG. 5 is a bottom view of the headset illustrating the location of the "on/off" switch 10 on the bottom of the leer earcup 58. A lip 11, which holds the battery in place, is also illustrated.

FIG. 6 illustrates the top 12, side 13, and front 14 of the rechargeable battery pack 2. The side of the battery pack is textured 15 to provide a grip for removing the pack from the head cup. As can be seen it is of an overall rectangular shape. Notch 15*a* interacts with latch 6 to hold the battery pack in place.

The assembly details of the headset are illustrated in FIG. 7 through FIG. 11.

Figure 7:
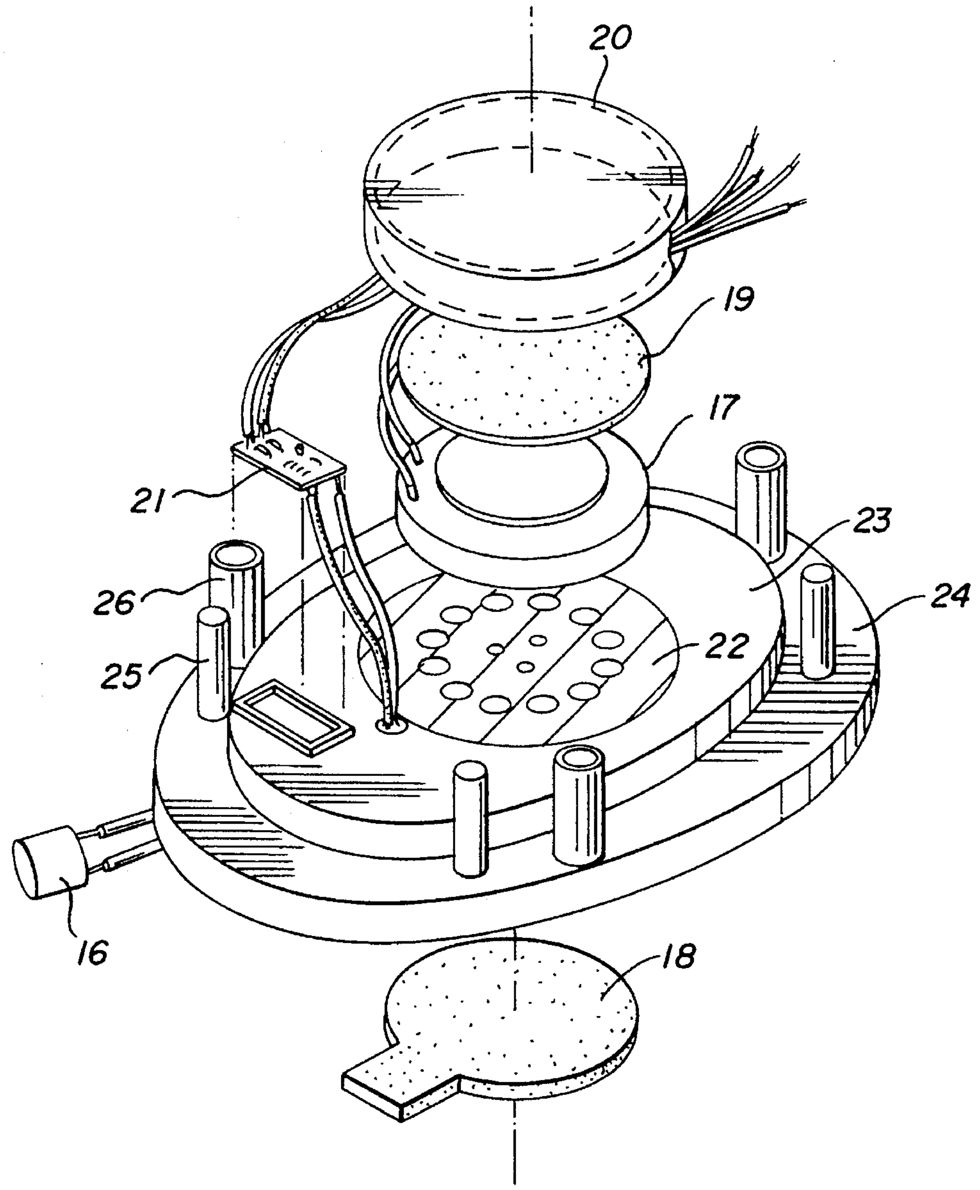

FIG. 7 illustrates the detailed assembly of the active section of each earcup. The active assembly includes a broad band omni directional microphone 16 such as an electret microphone or a micro machined silicone microphone. The choice of an omni directional microphone allows the orientation of the microphone relative to the speaker element 17 to be arbitrary, with the exception that the distance between the microphone and the speaker should be minimized to reduce the relative phase difference between the microphone and the speaker. In the instant invention the microphone is angled at 15° to 20° from the perpendicular of the driver membrane vibration. The microphone is also chosen to have a very broad frequency response (50 Hz to 20 KHz). This will assure that the phase response of the microphone is linear over the frequency band where noise is to be reduced. A piece of low density foam 18 is placed over the speaker to obscure the active elements from view. The speaker is backed with a foam section 19 to provide acoustic damping. A hollow and open cap 20 is then placed over the speaker which forms a back acoustic cavity. The combination of the foam 19 and cap 20 provides a means for making the response of the speaker more linear with frequency. The speaker drive circuitry is located on a small printed circuit board 21 and is identical for both left and right earcups. Holes 22 are cut in the upper level 23 of the active assembly to minimize coupling losses between the microphone and the speaker. The lower level portion 24 provides a surface for mounting the earcup seals and supports the separation bushings 25, 26 used for securing the PCBs and mechanically assembling the earcups.

Figure 8:
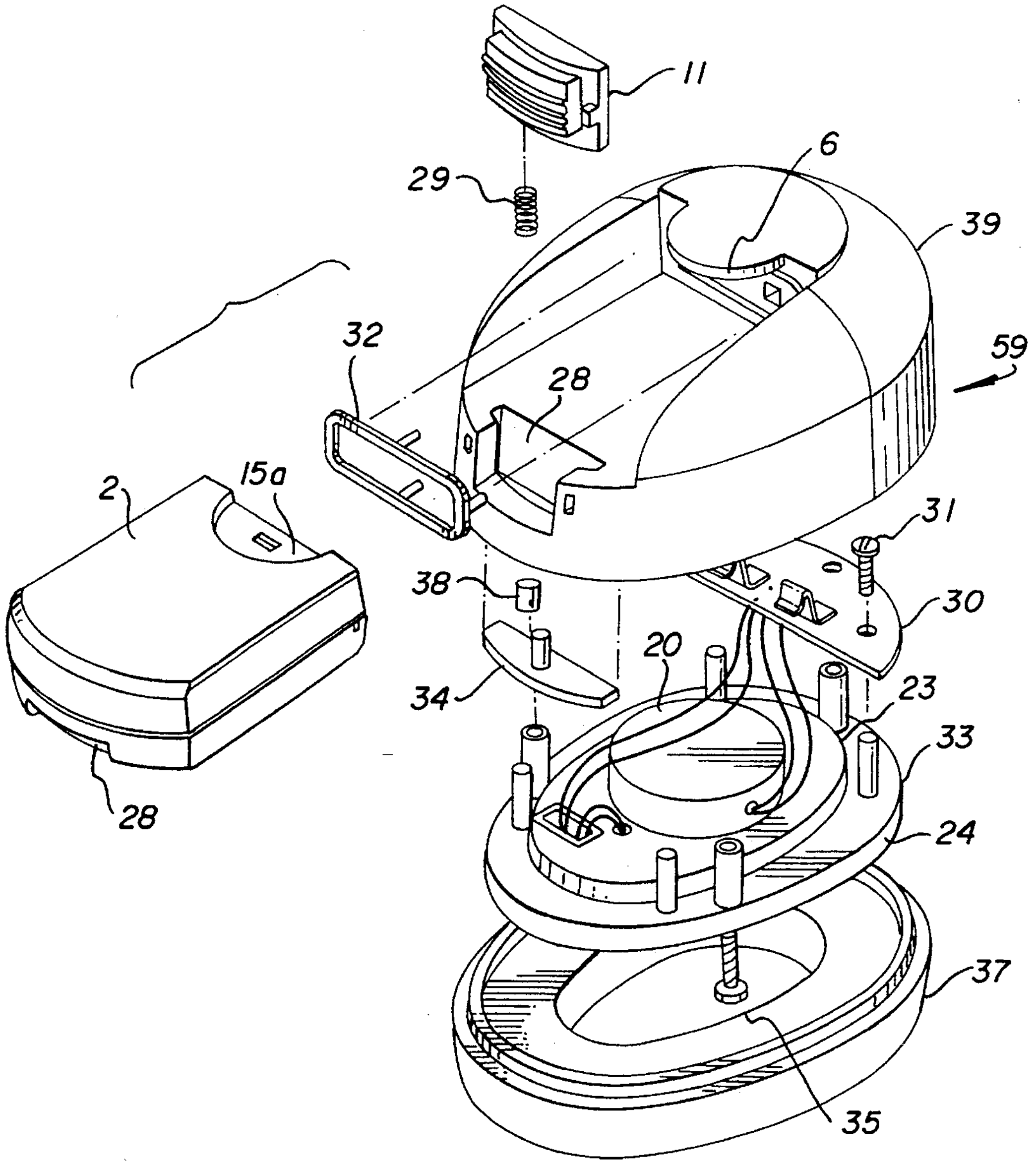

FIG. 8 illustrates the assembly of the right ear cup which houses the removable, rechargeable battery pack 2. A latch 11 and spring 29 assembly holds the battery pack in place through the interaction of lip 28 with latch 11. The right earcup 59 includes the printed wiring board 30 that holds the battery management system and the voltage multiplier. This PCB is mounted to the back of the active assembly 33 with portion 24 with two screws 31. An O-ring seal 32 is placed in front of the battery pack to prevent moisture from getting into the earcup or onto the battery terminals. The latch 11 is also sealed with a plastic cap 34 which is ultrasonically welded to the inside of the ear cup 59. Screws 35 are used to mount the active assembly securely into the earcup shell 36 which is injection molded from ABS. Inserts 37 are ultrasonically inserted to the completed assembly. An ear seal 37 is placed on the end of the cup to minimize noise entering the ear through the interface between the cup and the side of the user's head. This seal can be made of silicon gel or other suitable cushioning means that provide a seal around the ear.

Figure 9:
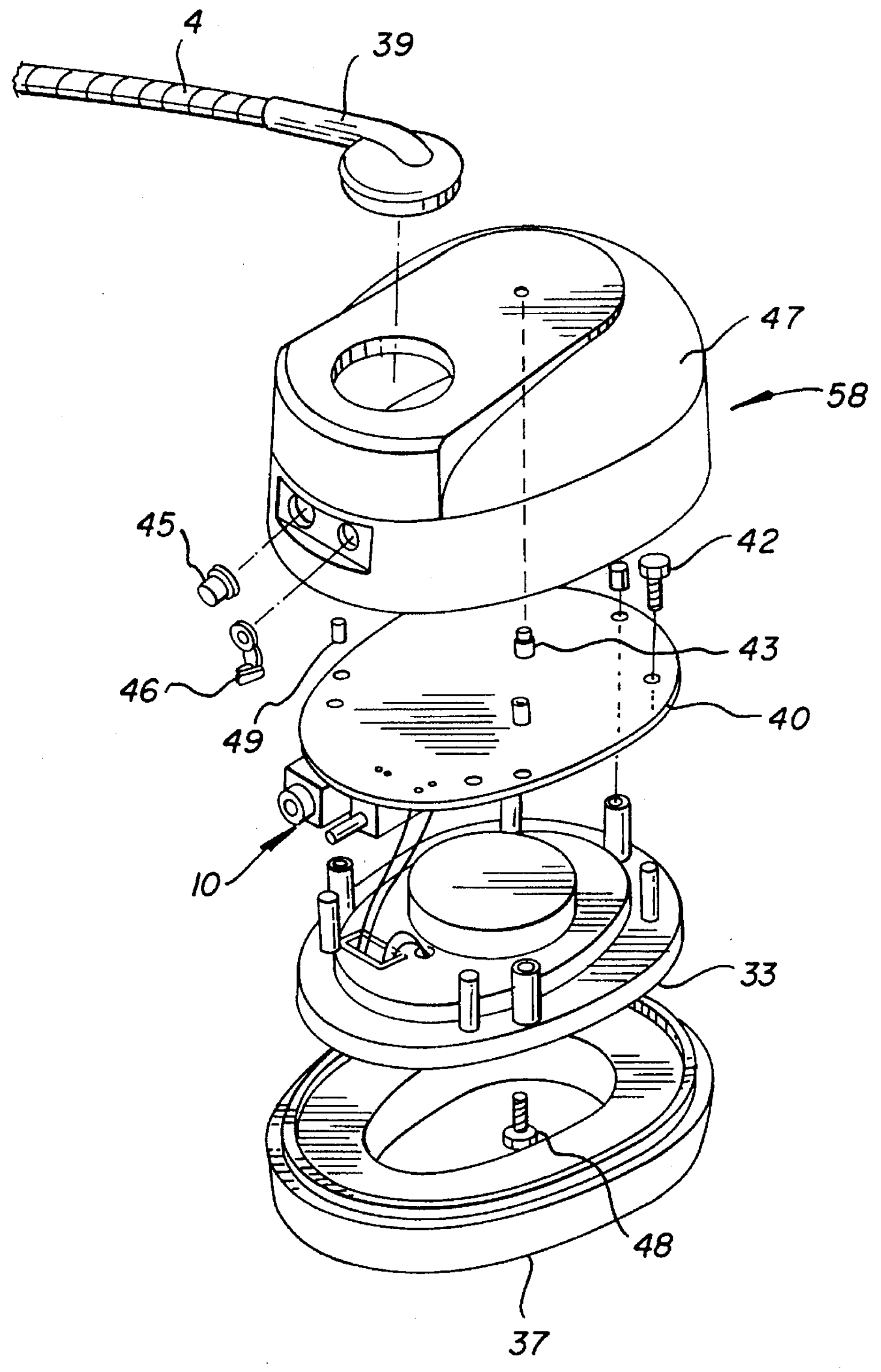

FIG. 9 illustrates the assembly of the left earcup 58, which includes the boom microphone 4 and the main printed circuit board (PCB) 40 which contains the noise cancellation circuitry for both earcups and the input jack for the boom microphone. A swivel attachment 39 allows for boom 4 to swivel through 45°. This PCB is mounted to the active assembly 33 with four screws 42. A light emitting diode (LED) 43 is mounted on the PCB to indicate when the power is turned on. This is shown in FIG. 3 also. The power is controlled by a push button switch 10 that is mounted to the PCB. A power button cover 45 is placed over the switch from outside the earcup 58 to reduce the chance of moisture entering the earcup. A port cover 46 is placed over the input jack to the boom microphone to prevent moisture penetration. The active assembly is mounted to the ear cup shell 47 with screws 48. Inserts 49 are ultrasonically inserted to the completed assembly. An ear seal 37 is placed on the end of the cup to minimize noise entering the ear through the interface between the cup and the side of the user's head.

Figure 10:
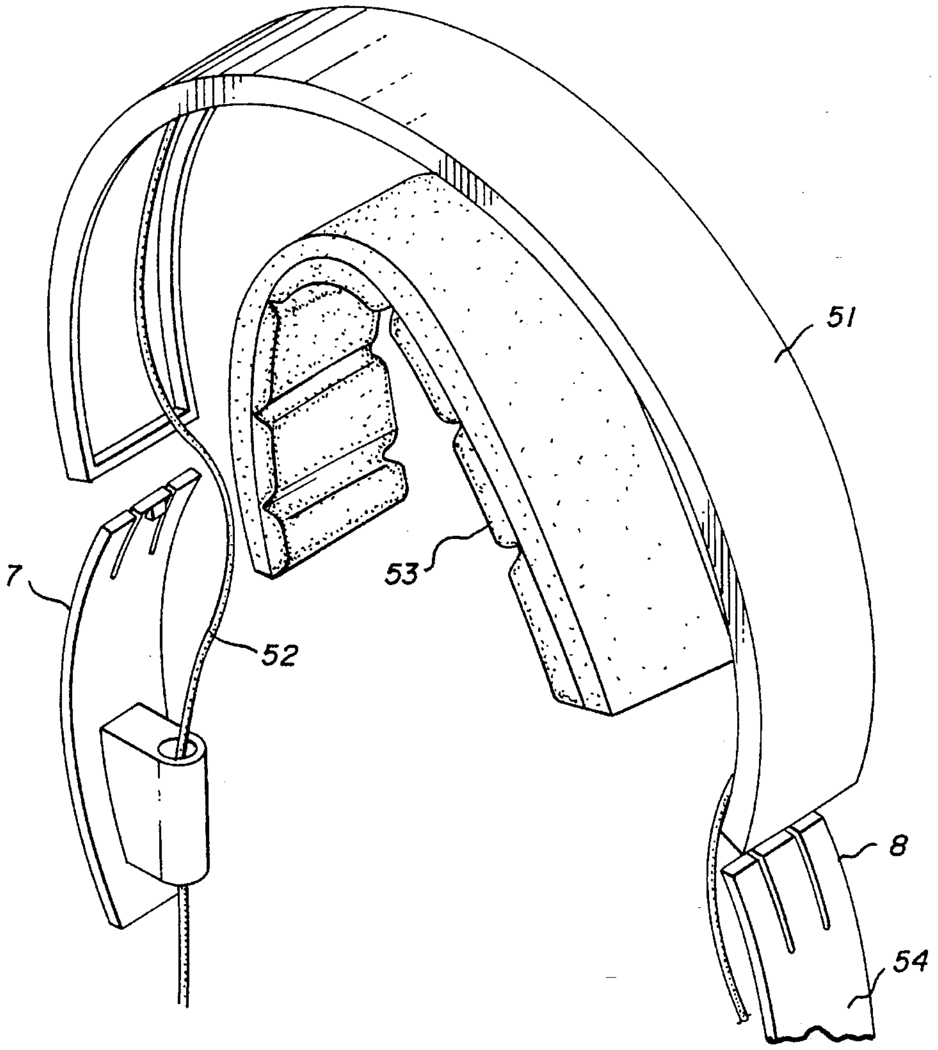

In FIG. 10 the assembly of the head band 51 is illustrated showing wires 52 being obscured in the under side of the head band behind the foam head pad 53, and the attachment of the head pad and the upper portion of the yokes 54 that support the earcups. The head pad is made replaceable for sanitary considerations.

Figure 11:
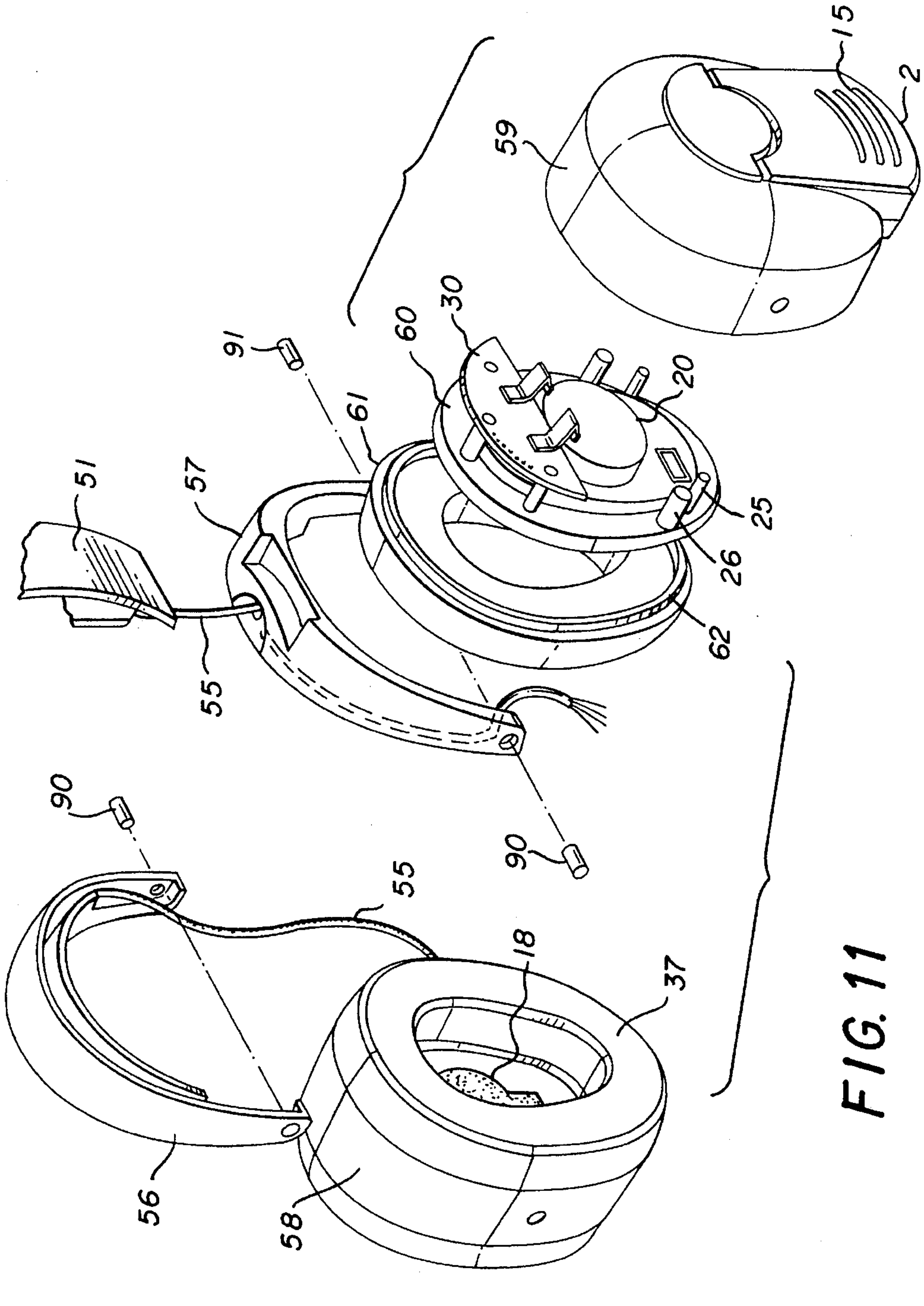

FIG. 11 shows the lower assembly of the headset further illustrating the technique for obscuring the wiring 55 by running the wires through the yokes 56, 57 and down inside the earcups 58, 59. FIG. 11 details the assembly of the right earcup, active noise control assembly 60 (same as left earcup) and the attachment to the head band 51 via the yoke 57. Also shown is the attachment of the ear seal 61, which is achieved through a mechanical locking mechanism to the inside of the earcup shell 59. The ear seals 37, 61 like head pad 53 are made replaceable for sanitation reasons. The ear seals have an annular locking groove 62.

Figure 12:
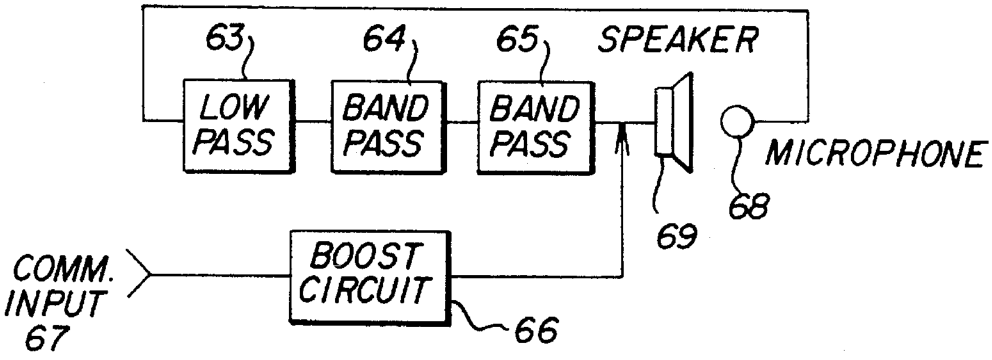
Figure 13:
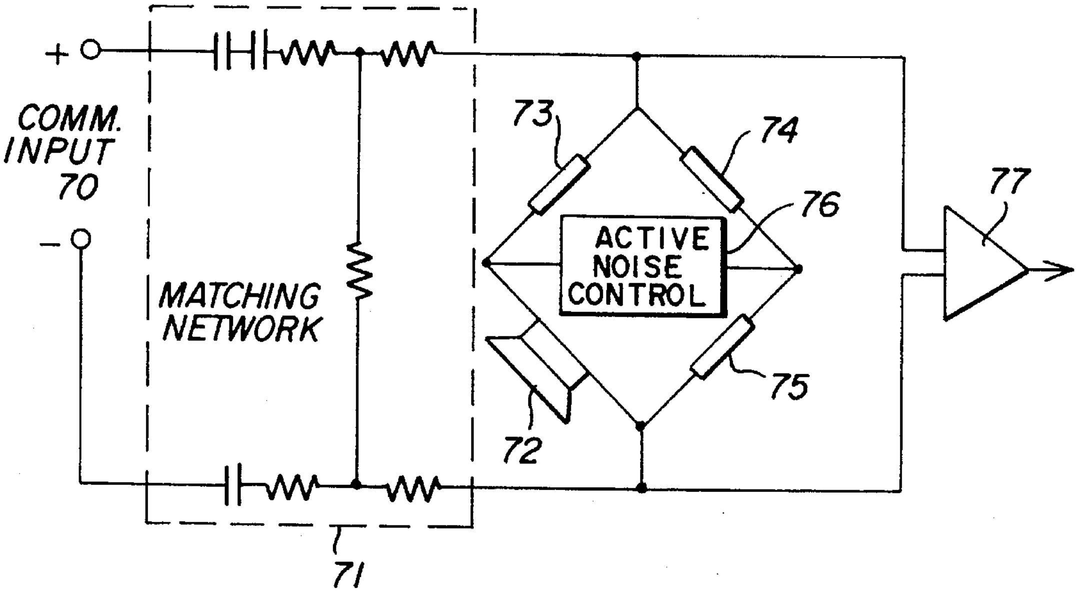

The electronics for the proposed head set are illustrated in FIGS. 12 and 13.

A block diagram of the electronic design is illustrated in FIG. 12. This figure illustrates the cascade of low pass 63 and band pass 64, 65 stages of the signal conditioning segments of the noise cancellation system. The low pass filter is essentially a single operational amplifier with the appropriate resistors and capacitors. The band pass filters are variable state filters consisting of four operational amplifiers and the appropriate resistors and capacitors. The boost circuit 66 that provides compensation to the communication signal 67 is also shown. The booster circuit consists of two operational amplifiers and appropriate resistors and capacitors which compensates for any signal loss resulting from the addition of anti-noise in the communication band. The microphone 68 and the speaker 69 make up the essential elements of the electro-acoustic feedback loop. The choice of an omni-directional microphone allows for an arbitrary placement of the microphone 68, with the exception that the microphone should be placed as close to the speaker as possible to minimize the phase difference between the microphone 68 and the speaker 69, since this phase difference represents a non-invertable time delay in the system transfer function. By choosing a very broad band microphone to assure linearity in phase and by placing the foam filled cavity behind the speaker to improve the linearity of the speaker, the remaining non linearity in the systems are compensated for by adjusting the properties of the low pass 63, and the band pass filters 64, 65. The properties of the low pass and band pass filters are adjusted by changing the values of resistors and capacitors in the each of the filters.

FIG. 13 illustrates the bridge circuit used to drive the speakers without interruption. The audio input from the communication system 70 is driven into a matching network 71 and then into a bridge circuit made up of the speaker 72 and the bridge balancing resistors 73, 74, and 75. The final output is fed into the boost circuit 77 referenced in Figure 12. The circuit allows the communication system to be operated when the active noise control circuitry 76 is turned off, and to override the active noise control circuitry when noise cancellation is in operation.

Figures 14, 14A:
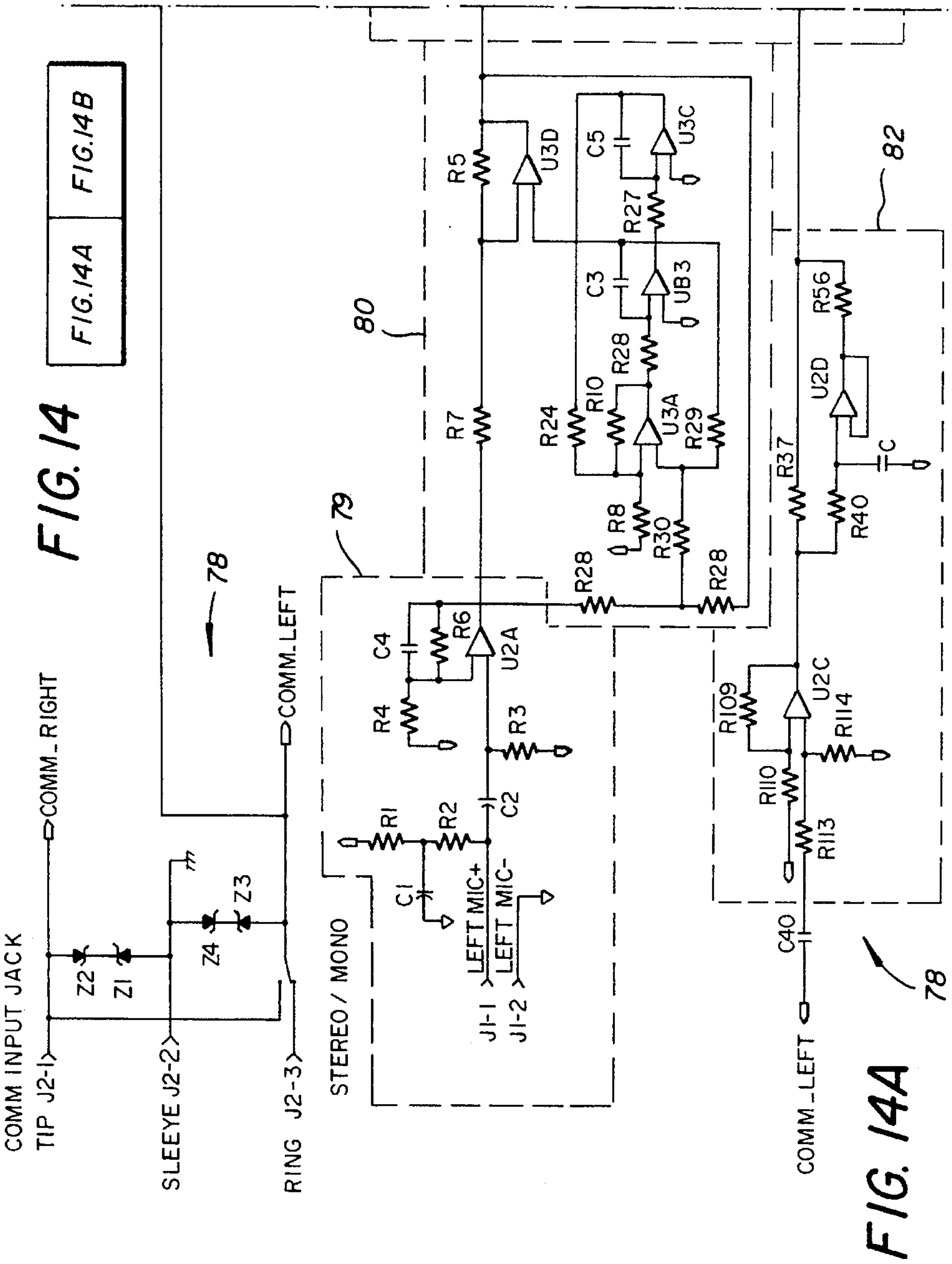
Figure 14B:
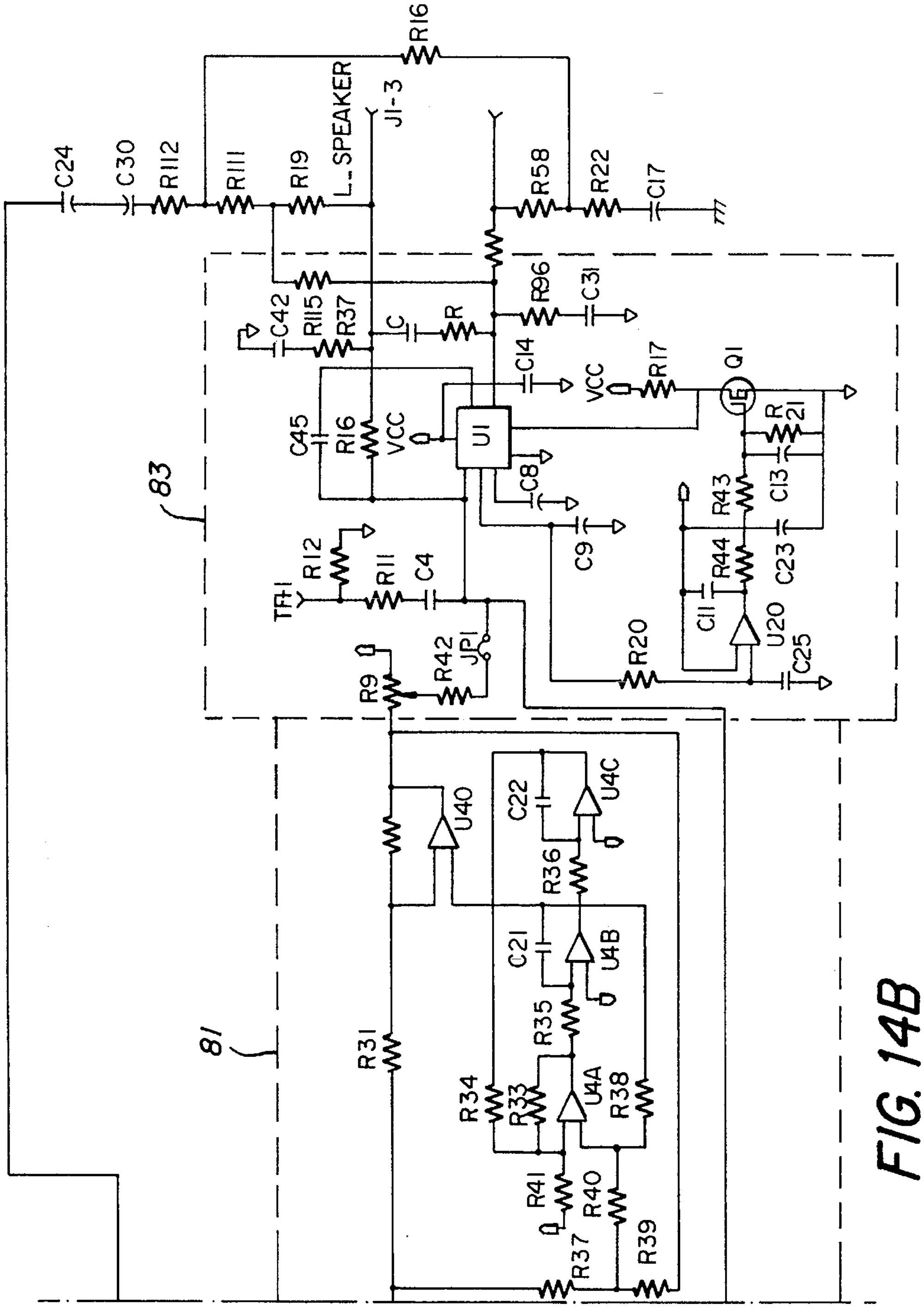

A detailed implementation of this electronic design for the left side of the headset is illustrated in FIG. 14. The right side is essentially identical to the left. The stereo/mono communication input 76 is shown feeding directly into the speaker drive circuitry and into the boost circuitry. The microphone input is fed directly into the low pass filter 77 where it is then fed to the two band pass filters 78 and 79. The use of the variable state filters allows for independent fine tuning of the gain, bandwidth, and center frequency of the two band pass filters. Tuning is achieved though changing the values of the discrete elements in each stage of the circuit. Each stage will be uniquely tuned to account for the various acoustic properties of the headset assembly, the speakers, and microphones that make up the final headset design. The boost circuit 80, and the speaker driver circuit 81 are also illustrated in FIG. 14.

Having described the invention with its innovative features it will be obvious to those of ordinary skill in the art that various changes and modifications can be made without departing from the scope of the appended claims.

We claim:

1. An improved communications headset which provides active noise cancellation without interruption of normal communication function, said headset comprising support means to allow a user to support the headset on his head, speaker means on said support means, communications means on said support means allowing the wearer to communicate remotely with others, active noise cancellation means on said support means, electronic control means on said support means which allows said wearer to employ said communication means with or without said active noise cancellation means, said electronic control means including an acoustic feed back circuit means with a booster circuit means to compensate for any low frequency losses in the communication signal due to operation of the active noise cancellation means and wherein said electronic control means includes a bridge Circuit means that allows for by-pass of said active noise cancellation means without affecting operation of said communication means and to override the active noise cancellation means when it is in operation.

2. A headset as in claim 1 wherein said acoustic feedback circuit means includes low pass and band pass filters.

3. An improved communications headset which provides active noise cancellation without interruption of normal communication function, said headset comprising support means to allow a user to support the headset on his head, speaker means on said support means, communications means on said support means allowing the wearer to communicate remotely with others, active noise cancellation means on said support means, electronic control means on said support means which allows said wearer to employ said communication means with or without said active noise cancellation means, and wherein said electronic control means includes a bridge circuit mean that allows for by-pass of said active noise cancellation means without affecting operation of said communication means and to override the active noise cancellation means when it is in operation, said speaker means is connected to both said communications means and to said active noise cancellation means and has a vibratable diaphragm and an acoustic cavity located rearward of said diaphragm which is filled with acoustically damping foam for enhanced noise cancellation, and wherein further said noise cancellation means includes at least one omni-directional microphone means.

4. A headset as in claim 3 wherein said speaker means and said omni-directional microphone means are located close to one another so as to minimize coupling losses.

5. A headset as in claim 3 wherein said microphone has a broad frequency response so that its response is always linear.

6. A headset as in claim 5 wherein said frequency response of the microphone is from 50 Hz to 20 KHz.

7. An improved communications headset which provides active noise cancellation without interruption of normal communication function, said headset comprising support means to allow a user to support the headset on his head, speaker means on said support means, communications means on said support means allowing the wearer to communicate remotely with others, active noise cancellation means on said support means, electronic control means on said support means which allows said wearer to employ said communication means with or without said active noise cancellation means, wherein said electron control means has filter means adapted to control bandwidth, center frequency, and gain to allow for fine tuning of the control system and wherein said electronic control means includes a bridge circuit means that allows for by-pass of said active noise cancellation means without affecting operation of said communication means and to override the active noise cancellation means when it is in operation.

8. An improved communications headset which provides active noise cancellation without interruption of normal communication function, said headset comprising support means to allow a user to support the headset on his head, speaker means on said support means, communications means on said support means allowing the wearer to communicate remotely with others, active noise cancellation means on said support means, electronic control means on said support means which allows said wearer to employ said communication means with or without said active noise cancellation means, wherein said electronic control means is adapted to compensate for any losses in a communication system due to operation of said active noise cancellation, wherein said electronic control means includes tunable variable mode filter means with switching capacitors for fine tuning and wherein said electronic control means includes a bridge circuit means that allows for by-pass of said active noise cancellation means without affecting operation of said communication means and to override the active noise cancellation means when it in operation.

9. An active noise cancellation headset to provide attenuation of unwanted noise in a given environment, said headset comprising a head support assembly means adapted to fit atop the wearer's head, at least one earcup means having a front cavity on said assembly means and adapted to overlie a wearer's ear, speaker means adjacent said front cavity and adapted to be driven to cancel unwanted noise, circuit means within said assembly means adapted to drive said speaker means to produce counter noise, an omni directional microphone means acoustically close coupled within said front cavity so as to minimize the phase difference between said speaker and microphone means, said microphone means adapted to feed a residual signal representing the summation of the unwanted noise and counter noise to said circuit means, and back cavity means adjacent said speaker means and adapted to make the speaker means linear with frequency to provide active noise cancellation over a broad range of frequencies, and including a second earcup means having a speaker means, back cavity means, circuit means and microphone means configured the same as those elements in said first earcup means, and wherein said headset additionally includes a two-way communications system and said circuit means and said speaker means are adapted to handle both communications signals and counter-noise signals, and wherein said circuit means includes a bridge circuit which allows for a wearer to use said communications system alone or with said active noise cancellation operative, and wherein said circuit means additionally includes an acoustic feedback circuit with a booster circuit to compensate for losses in the overall circuit when both the communications and said active noise reduction are used simultaneously.

10. A headset as in claim 9 wherein both said earcups are open-backed.

11. A headset as in claim 9 wherein said acoustic feedback circuit includes low pass and band filters.

12. A headset as in claim 9 including digital processing means is used to fine tune the circuit means.

* * * * *